United States Patent [19]

Schemmel

[11] 4,088,315

[45] May 9, 1978

[54] DEVICE FOR SELF-DEFENSE TRAINING

[76] Inventor: Robert Archer Schemmel, 18012 Hiawatha St., Northridge, Calif. 91324

[21] Appl. No.: 707,361

[22] Filed: Jul. 21, 1976

[51] Int. Cl.² ............................................. A63B 69/00
[52] U.S. Cl. ...................................................... 272/76
[58] Field of Search ....................... 272/76, 77, 78, 98; 273/55 R, 55 A, 1 F

[56] References Cited

U.S. PATENT DOCUMENTS

| 2,909,370 | 10/1959 | Fortney | 272/76 |
| 3,250,533 | 5/1966 | Nicholson | 272/76 |
| 3,804,406 | 4/1974 | Viscione | 272/76 |

FOREIGN PATENT DOCUMENTS

| 2,232,039 | 1/1973 | Germany | 272/76 |
| 380,371 | 7/1922 | Germany | 272/76 |
| 641,618 | 6/1937 | Germany | 272/76 |
| 600,059 | 3/1948 | United Kingdom | 272/76 |
| 141,691 | 3/1961 | U.S.S.R. | 272/76 |

Primary Examiner—William H. Grieb
Assistant Examiner—T. Brown
Attorney, Agent, or Firm—John J. Posta, Jr.

[57] ABSTRACT

An improved device for use in self defense training, as in karate and the like, includes a life-like articulated training dummy supported in an upright position on a post and having a plurality of separate pressure receptors disposed at various target locations in the dummy. The receptors are interconnected to a signal such as individual lights in a remote display panel so that hits on the receptors can be separately displayed by the panel. The panel can include a timer, hit sequence counter, hit sequence programmer, printed readout, and hit sequence replayer, as well as a warning signal, visual and/or audible, and other safety and training aids. The receptors can be made to distinguish between light and heavy blows. The support post can be rotated at high speed to cause the dummy to simulate an attack when activated by weight detectors in a base around the post. The weight detectors are also disposable in the base in a mode to facilitate stance training. The dummy and post can be provided with shock absorbing elements to protect them from heavy hits during practice. Preferably the dummy includes a tough, resilient surface layer for further protection of the dummy and trainee (one using the dummy) and for toughening the hands of the trainee. The device provides unique advantages in the art of self defense training.

29 Claims, 14 Drawing Figures

DEVICE FOR SELF-DEFENSE TRAINING

BACKGROUND OF THE INVENTION

1. Field of the Invention

The present invention generally relates to training aids and more particularly to an improved device for use in self defense training, as in karate, judo and the like.

2. Prior Art

In the art of self defense, such as karate, judo and the like, the classical approach has been to practice self defense techniques with a training partner, using either no body contact at all or some degree of contact, such as full contact, but with a range of padding accessories worn by both partners in order to protect both partners against injury. If no partner is available, then one usually practices on a stuffed hanging canvass bag or a stuffed blocking dummy or the like.

None of the above techniques optimizes self defense practice in that in no instance can one practice actually hitting an unprotected individual as hard as possible in all the desired body locations so as to instantly inflict what would be a mortal or disabling blow. Therefore, what is needed in this art is an essentially indestructible practice person, capable of indicating lethal and disabling blows and yet durable.

SUMMARY OF THE INVENTION

The foregoing needs have now been satisfied by providing the improved training device of the present invention. The device is substantially as set forth in the Abstract above.

Thus, it includes a practice dummy which preferably has the appearance, configuration, size and feel of a human adversary, and which is equipped with a series of separate pressure receptors generally disposed just below the surface thereof at target locations, such as the neck, kidneys, eyes, temples, arms, legs, solar plexus, mid-section, jaw and groin. These receptors are interconnected with signaling means which preferably are remotely located in a display panel and are adapted to signal, as by lights, when hits are made on the receptors. The receptors can be made to discriminate between light and heavy blows and signal the same; as by different colored display lights, etc.

The dummy is supported in an upright position on a telescoping, flexible, preferably rotatable, post disposed on a base. The dummy has articulated joints and can be placed in and then locked in various body and limb positions to realistically depict a human adversary in various postures of defense and attack. The dummy and post can be protected against damage during use by shock absorbers, padded areas (as in the neck region), etc.

The base can be divided into a plurality of separate independent segments, each with its own weight detector, interconnected with the display panel signaling means, etc., for example, to facilitate detection of weight differences and thus aid the practice of proper balance and stance. The rotatable dummy can also be programmed through control means connected to the weight detectors and power means to turn rapidly towards a person standing on a given base segment in order to simulate an attack.

Suitable safety cut-out means may be incorporated to prevent collision with the turning dummy. Standing on the base can also be made to elicit a signal from the display panel warning of an impending attack, etc.

The display panel can incorporate a timer, hit counter, printed readout and sequence replayer. Programming means may be incorporated into the display panel so that the operator can establish a hit sequence which must be followed in a specified time, and the means to verify that it is followed. The programming means also enables an instructor to demonstrate visually and/or audibly via the display panel a desired hit sequence before it is practiced by the trainee on the dummy. Further features of the present invention are set forth in the following detailed description and accompanying drawings.

DETAILED DESCRIPTION

FIGS. 1, 2, 3 and 4

Figure 1:
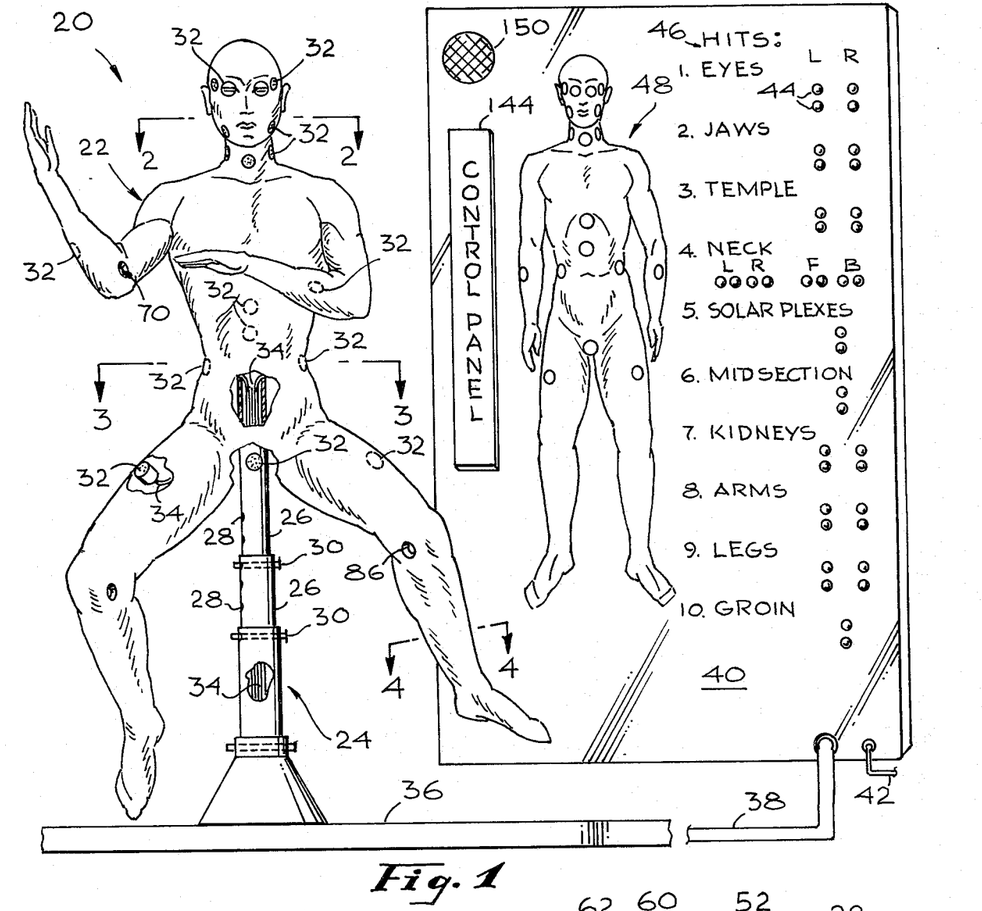
FIG. 1 is a schematic front elevation of a first preferred embodiment of the improved training device of the present invention, illustrating a man-like dummy interconnected through support means with a display and control panel.

Now referring more particularly to FIG. 1 of the accompanying drawings, a preferred embodiment of the self defense training device of the present invention is schematically depicted therein. Thus, a device 20 is shown which includes a dummy preferably having the appearance, configuration, size and feel of a man. Dummy 22 is supported in a generally upright position by a flexible vertical post 24 of metal or the like having a plurality of telescoping sections 26, each of which may include means to lock the sections 26 together at any given degree of extension, for example, horizontally aligned spaced pairs of apertures 28 through which pins 30 may be removably inserted to releasably hold dummy 22 at the desired height. Thus, for example, post 24 may be fully extended to raise dummy 22 when it is desired to practice or practice against certain training exercises such as high leg kicks, etc.

Dummy 22 has a plurality of separate pressure responsive receptors 32 located at target points, such as at both temples, the eyes, the jaws, the front, back and sides of the neck, the solar plexus, stomach, groin, kidneys, arms and legs of dummy 22. Receptors 32 preferably are disposed generally close to the outer surface of dummy 22, and are interconnected, as by electrical wiring 34 running down through dummy and post 34, through base 36, around post 24 and through conduit 38, to an electrical display panel 40. Panel 40 is in turn connected with an electrical source, as through an electrical card 42. Panel 40 includes signaling means, such as display lights 44 associated with indicia in the form of written indicia or labeling 46 and a schematic figure 48 representing dummy 22 to indicate the location and nature of each hit made by a trainee on any given receptor 32 of dummy 22 when panel 40 is turned on.

Figures 2, 3, 4:
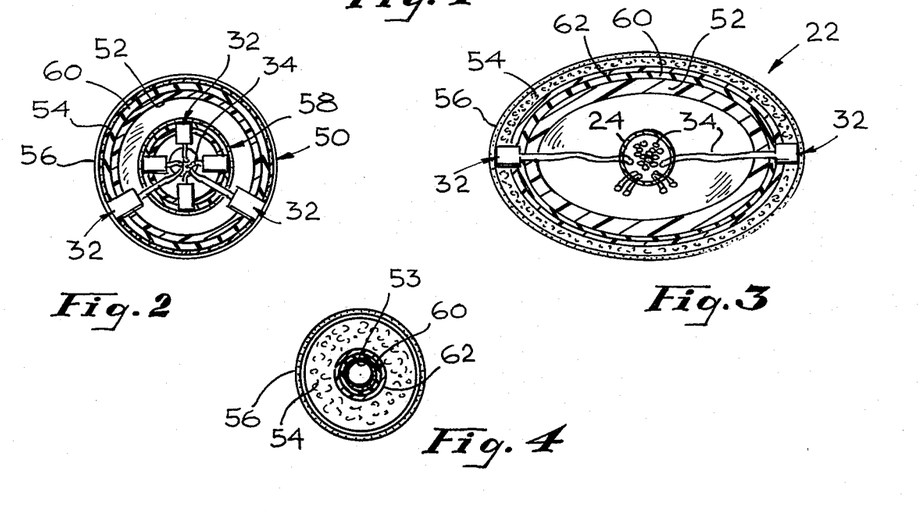
FIG. 2 is a schematic cross-section taken along the section line 2—2 of FIG. 1.
FIG. 3 is a schematic cross-section taken along the section line 3—3 of FIG. 1.
FIG. 4 is a schematic cross-section taken along the section line 4—4 of FIG. 1.

The construction of dummy 22 is such as to readily withstand striking of the dummy and receptors 32 thereof by the hands, knuckles, elbows, arms, legs, feet, etc. in practicing self defense using the dummy 22. Thus, as shown in FIG. 2, the head 50 of dummy 22 may comprise a hard skull 52 of nylon, plastic or the like over which may be provided a thin layer 54 of resilient rubber padding or the like, in turn enclosed within a skin-like outer layer 56 of tough, flexible canvass, plastic or the like. The trainee's hands can be toughened by repeatedly striking blows on layer 56. Wiring 34 from neck receptors 32 is also shown in FIG. 2 running down through narrowed neck region 58 into the trunk of dummy 22.

FIG. 3 is a section through the waist region of dummy 22 showing nylon core 52 which is an extension of skull 52, (and a neck core, not shown) and is enclosed, for example, in a rubber sleeve 60, which in turn may be enclosed in a nylon sleeve 62 disposed within a layer of rubber padding 54 within an outer skin 56 of canvass. FIG. 3 shows kidneys receptors 32 and wiring 34 from those and other receptors passing down into post 24.

FIG. 4 is a section through a lower leg of dummy 22 and shows a hollow tube card 52 of nylon, steel or the like covered with a rubber sleeve 60 overlaid with nylon sleeve 62 and enclosed in rubber padding 54 and an outer skin 56 of canvass. No receptors 32 or wiring 34 are present at that level in dummy 22's leg. It will be understood that other arrangements and combinations of components can be used to protect dummy 22 and the trainee using the same.

Figures 5, 6, 8, 9:
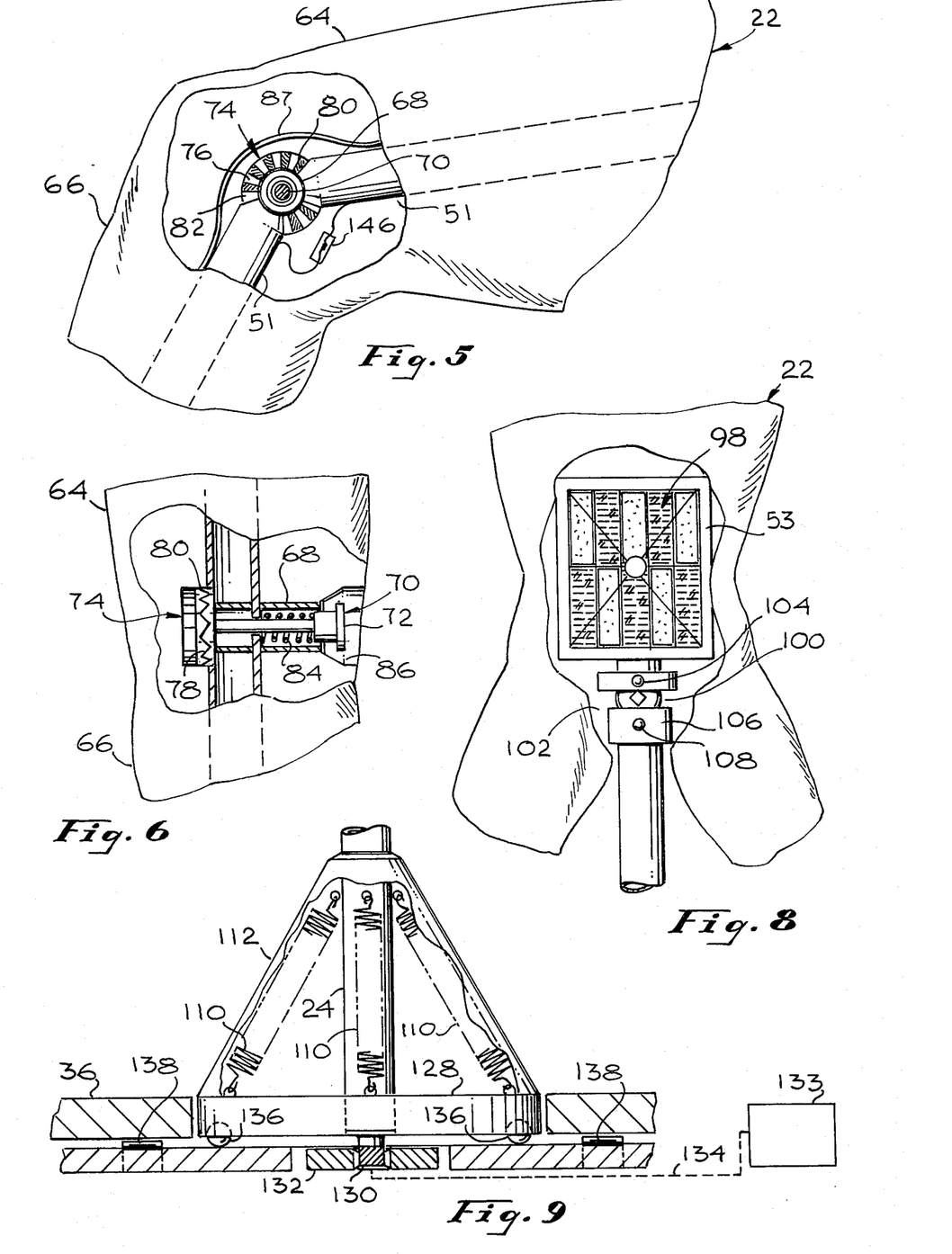
FIG. 5 is an enlarged schematic side elevation of a portion of a leg of the dummy of FIG. 1, portions being broken away to illustrate certain internal features.
FIG. 6 is a schematic front elevation of the leg of FIG. 5, portions being broken away to illustrate certain internal features.
FIG. 8 is a schematic front elevation of the lower torso and upper leg portion of a modified version of the dummy of FIG. 1, portions being broken away to illustrate certain internal features, particularly shock absorbing means.
FIG. 9 is a schematic front elevation of the lower end of the post of FIG. 1, and the base of FIG. 1, portions being broken away to illustrate internal shock absorbers and other features.

FIG. 5 and 6

Dummy 22 has movable and lockable articulated joints, such as are shown in FIGS. 5 and 6. Thus, in FIG. 5, there is shown in schematic side elevation an upper leg 64 of dummy 22 which is tongue and groove joined to lower leg 66 for rotation of the latter relative thertho. A transverse tube 68 is disposed, as shown in FIG. 5, through legs 64 and 66 adjacent to or at the juncture line or pivot point thereof. Tube 68 thus can act as a pivot pin for legs 64 and 66. Moreover, it bears means to releasably lock legs 64 and 66 in any given position. Thus, it has a plunger 70 extending therethrough, one end of which is formed into an expanded release knob 72. The opposite end of plunger 70 is formed into a lock 70 having a configured inner face 76 which is adapted to mate with a catch 78 secured to the outer surface of tube 68. Lock 74 also bears a knurled leading edge 80 which is adapted to simultaneously engage spaced detents 82 in legs 64 and 66 to help releasably lock the two legs in place.

Plunger 70 is biased into the locked position by a spring 84. When it is desired to unlock legs 64 and 66 in order to move them to a new position, knob 72 is depressed, and is held depressed while leg 66 is rotated relative to leg 64. Knob 72 is then released to cause edges 80 to engage detents 82 and lock leg 66 in place. It will be noted that knob 72 is disposed in a pocket 86 to protect the trainee against injury on knob 72 and also to prevent inadvertent unlocking of leg 66. It will be understood that any other suitable releasable locking mechanism can be used, if desired.

It will be further understood that dummy 22 has similar movable articulations at the points of junction between the legs and trunk, upper and lower arms, and upper arms and trunk as well as others, as may be desired to impart the desired positional effects.

Moreover, wiring running through cores 52 can bridge joints, as those between the upper and lower arms and those between the upper and lower legs, by passing from one core 52 into a flexible bridging cable 87 (FIG. 5) and then across the joint and into the next core 52, and thus continuing through dummy 22 and into post 24.

Figures 7, 10, 11, 12, 13:
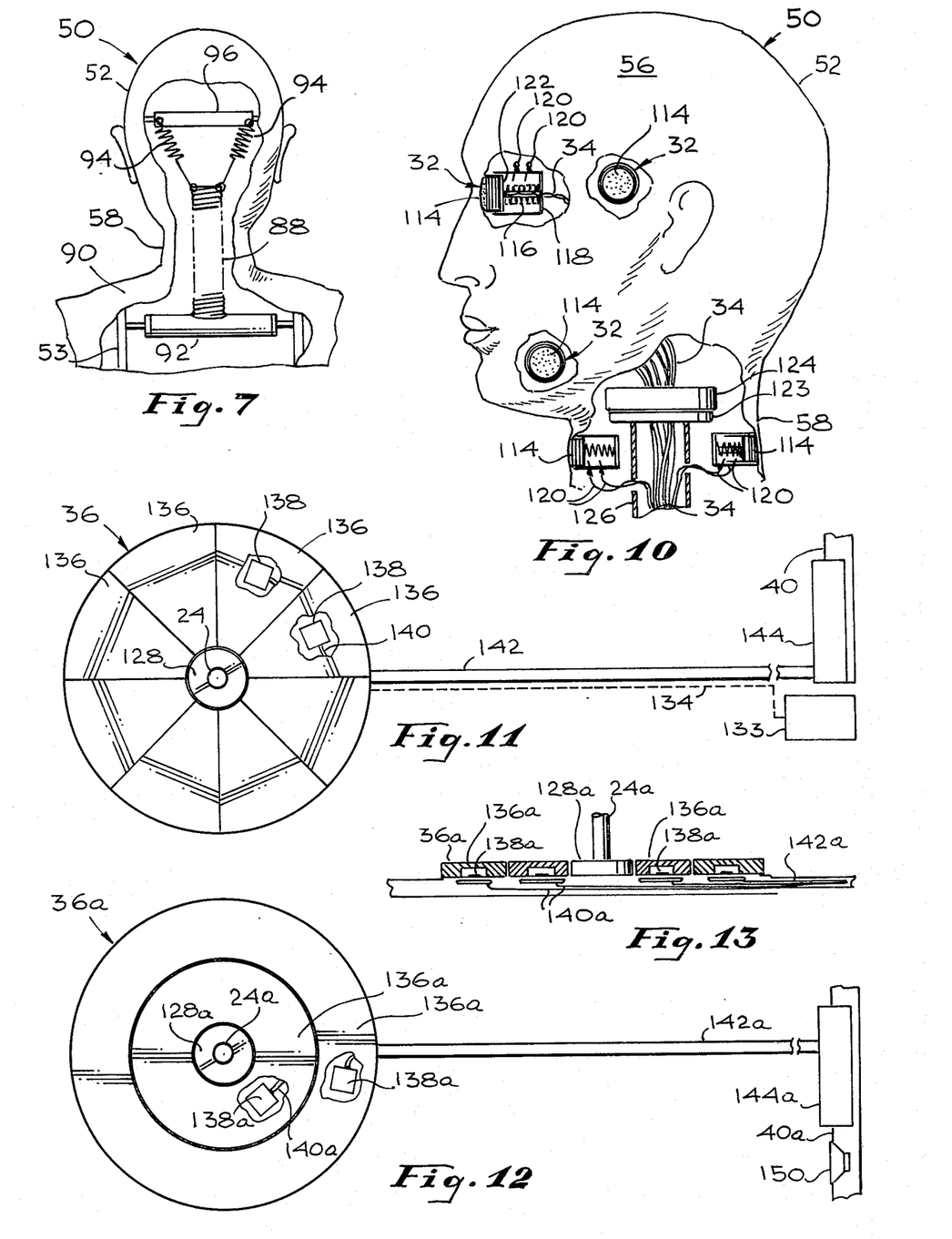
FIG. 7 is a schematic rear elevation of the head, neck and upper thoracic portion of a modified version of the dummy of FIG. 1, portions being broken away to illustrate certain internal features, particularly shock absorbing means.
FIG. 10 is a schematic side elevation of the head and upper neck region of a modified version of the dummy of FIG. 1, portions being broken away to illustrate certain internal features.
FIG. 11 is a schematic top plan view of the base portion of the device of FIG. 1, portions being broken away to illustrate certain internal features.
FIG. 12 is a schematic top plan view of a modification of the base of the present device, portions being broken away to illustrate certain internal features.
FIG. 13 is a schematic side elevation of the base of FIG. 12, portions being broken away to illustrate certain internal features; and, FIG. 14 is a schematic front elevation of the control panel portion of the display panel of FIG. 1.

FIG. 7 and 8

Dummy 22 can be further protected from damage during use through the application of spring, rubber, hydraulic or other types of shock absorbers at strategic locations. Preferably, for example, head 50 and neck 58 can be protected by a coiled spring 60 extending between head 50 and thorax 90, secured on and to a cross support 92 secured to frame 52 to thorax of dummy 22 and connected at its upper end to a pair 94 of springs, which are in turn connected to opposite sides of a cross brade 96 fixed in skull 52.

The lower portion and midsection of dummy 22 may also be well protected, as shown in FIG. 8, against midsection and groin kicks by a shock absorber 98 secured to frame 52 and to a universal joint 100 extending out behind the groin 102 in dummy 22. Joint 100 can be provided with a tilt lock mechanism 104 accessible through a cavity (not shown) in dummy 22 so that dummy 22 can be tilted and releasably locked in place through joint 100 in any desired position relative to post 24. Post 24 can have a rotating head 106 with a releasable lock pin 108, also accessible through said cavity (not shown) behind groin 102.

FIG. 9

Dummy 22 and post 24 are further protected from damage during use through the application of a set of spaced coiled spring shock absorbers 110 disposed within a cover 112 on four sides of post 24 and connected both to post 24 and to base 36, as shown in FIG. 9.

Base 36 may be relatively solid wood, metal or the like, is relatively heavy and extends horizontally some distance from post 24 to add stability to device 20 and to absorb shocks. Preferably, as previously mentioned, post 24 is made somewhat flexible, as of high tensile steel tubing or the like, to further absorb the shock of heavy leg kicks, butts, etc. delivered to dummy 22.

FIG. 10

Receptors 32 may be fabricated in any suitable form. For example, as shown in FIG. 10, in which head 50 and neck 58 are depicted, each receptor 32 may comprise a blow-receiving pad or layer 114 adjacent the surface 56 of dummy 22 and secured at its rear end to a coil spring 116. Spring 116 is held in place at its rear end by a support 118. At least one electrical contact 120 is disposed along the path of travel of layer 114 when it is hit by a blow, that is, towards support 118. The surface 122 of layer 114 adjacent contact 120 is electrically conductive and when surface 122 touches contact 120, an electrical circuit through wiring 34 and a given light 144 in panel 40 is completed, causing that light 44 to light up and identify the hit and its location. Moreover, in the embodiment shown in FIG. 10, a pair of contacts 120 are spaced along the described traveling path so that a separate light 44 interconnected to each contact 120 can be separately activated. This arrangement thus can indicate the force of the blow which has been delivered to and has moved layer 114, larger blows causing layer 114 to to more closely approach support 118, engage both contacts 120 and thus activate two lights 44 in panel 40 instead of one light 44. Lights 44 for light blows can be, if desired, of different color from those for stronger blows so that the difference can be instantly noted. It will also be understood that audible signals at panel 40 could be used in place of or in addition to lights 44.

Receptors 32 in FIG. 10 are shown in the eye, temple, jaw and neck regions, each with a separate set of wiring 34 leading to a separate pair of lights 44 in panel 40. FIG. 8 also shows that head 50 can be connected to neck 58 by a swivel joint 122 between a cross post 124 in head 50 and a vertical hollow tube core 126 extending between head 50 and neck 58. This modified construction permits dummy's head 50 to be placed in a desired target position and also tends to dissipate the force of glancing blows to head 50 by causing head 50 to rotate.

FIGS. 9, 11, 12 and 13

The entire dummy 22 preferably is turnable in order to give the trainee or exerciser practice in attack and defense against dummy 22 from various angles. Thus, for example, as shown in FIG. 9, post 24 can extend down through a central portion 128 of base 36 and terminate in a gear 130 mating with drive gear 132 powered by power means 133 through a drive shaft 134 extending from base 36. Through this arrangement, post 24 and dummy 22 can be made to turn rapidly in any desired direction, carrying with post 24 the portion 128, which is supported on rubber rollers 136 above the lowermost portion 138 of base 36. The remainder of base 36 can be divided for various purposes into a plurality of independent segments, as shown particularly in FIGS. 11, 12 and 13.

FIG. 11

Referring now more particularly to FIG. 11, base 36 is shown divided into eight independent segments 136 radiating from post 24 and control portion 128 of base 36. Each segment 136 is supported on a separate signal-transmitting weight detector 138 connected by separate wiring 140 through a common conduit, 142 (which may be the same as conduit 42) to control means 144 in panel 40 and indirectly to power means 133. Each detector 138 can be set to generate a signal when a predetermined weight load is on that detector. Control means 144 can be operated normally or automatically, with or without time delay, to cause post 24 and dummy 22 to turn rapidly (through power means 133, conduit 134 and gears 130 and 132) towards segment 136 the weight detector 138 of which indicates through its signal that the trainee is standing thereon. Thus, practice can be had in quickly reacting to a sudden attack. Details of control means 144 relative to this activity are set forth hereinafter.

In order to prevent a collision between an extended limb of dummy 22 as it rapidly turns, and a person in the path of dummy 22's extended limb, control means 144 can also include an automatic safety cut-out mechanism which will instantly switch off power means 133 if that situation is detected, for example, when control means 144 simultaneously receives a signal from a weight detector 138 in the turning path of dummy 22 and a signal from an extended limb detector 146, such as is schematically shown in FIG. 5. Detector 146 can, for example, include a pair of arms, one connected to each core 52 in the leg articulation region, the arms contacting and causing a signal only when cores 52 of the legs involved are at a predetermined angle. Other safety cut-out arrangements can also be provided in place of or in addition to those described.

FIGS. 12 and 13

It is important to be able to practice proper stance and balance in the art of self defense. This can easily be accomplished by utilizing the modification shown in FIGS. 12 and 13. The components which are generally similar to those previously described are designated with the same numerals but succeeded by the letter "a". Thus, base 36a is shown which is disposed around post 24a. Post 24a may be fixed or rotatable, either powered or unpowered. Base 36a is divided into two independent doughnut shaped circular segments 136a, one inside the other and both encircling post 24a. Each segment 136a is supported on a separate signaling weight detector 138a connected to panel 40a, particularly control means 144a thereof, by wiring 140a running through conduit 142a. Each weight detector 138a can put out a weries of signals to control means 144 to indicate the actual weight placed on the segment 136a disposed on it. Control means 144 can visually display the weight distribution between the two segments 136a and thus the stance of the trainee. The trainee stands with one foot on each segment 138a during practice. Contact means 144 is electrically connected to a signal horn 150 and can make horn 150 emit a signal when the distribution of weight between segments 136a is outside a predetermined presetable range and thus the stance is incorrect. Details of this feature are set forth hereinafter in a discussion of control means 144.

A simulated attack can easily be practiced, utilizing the modification of FIGS. 12 and 13. Thus, for example, control means 144 can be set to suddenly and randomly sound through horn 150 distinctive warning tone when the trainee is completely within the inner segment 136a. This is sensed by the presence of weight on that segment and no weight on the remaining segment 136a. A second distinctive signal from horn 150 can be made to sound, via control means 144, in the event that weight is not totally removed from the inner segment 136a within a predetermined time span, for example, 1 second.

Figure 14:
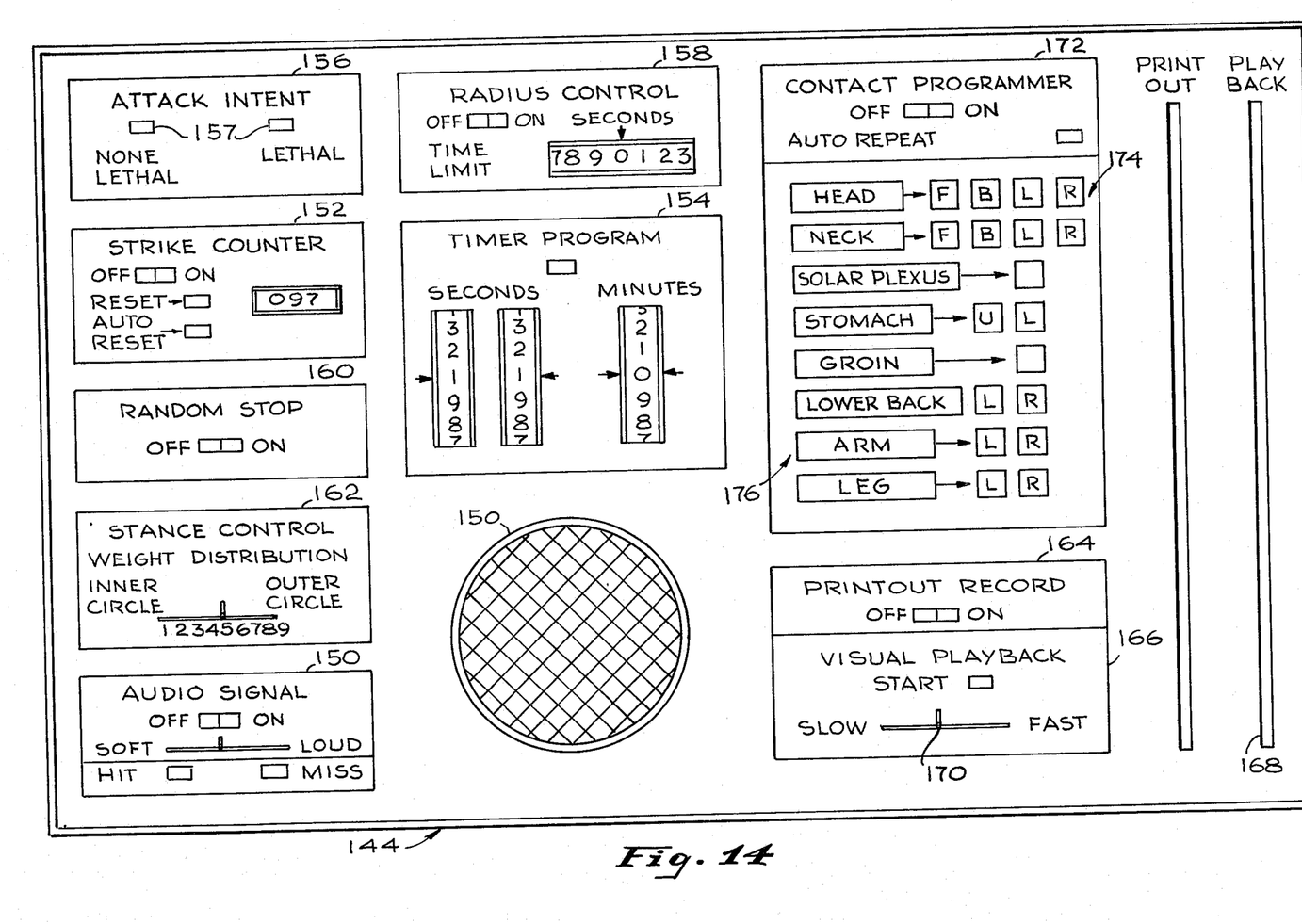

FIG. 14

Now referring more particularly to FIG. 14, control means or panel 144 in display panel 40 is shown in detail. It includes, in addition to horn 150 (audio signal which can be changed in tone and intensity), an electrically powered strike counter 152 and an electrically powered timer 154. The strike counter is a digital counter connected to pressure responsive receptors 32 in dummy 22 for counting the total number of strikes to all of receptors 32, after it is set manually or automatically. Timer 154 functions separately from the rest of panel 40 for timing exercises and practice sequences which do not require use of panel 40. Timer 154 can also be set to time exercises, such as the simulated attack and retreat previously described, as well as other programs. Moreover, timer 154 is integrated with counter 152, so as to be able to display hits/unit time in a separate display. Timer 154 is connected to an attack intent mechanism 156, in panel 144 which includes two programmed sequences, lethal and non-lethal. Both sequences are indicated by a signal from horn 150. The lethal sequence requires at least two strikes by the trainee on dummy 22 at lethal target points (neck, temples, etc.) within 3 seconds. Otherwise, a warning signal from horn 150 sounds. Thus, mechanism 156 is connected to receptors 32 and horn 150, as well as timer 154. The non-lethal sequence requires only strikes at non-lethal points on dummy 22, otherwise a warning signal is given. Buttons 157 determine which if either sequence is to be used.

Control panel 144 includes a radius control mechanism 158 which is connected to timer 154, receptors 32, horn 150 and base 36 weight receptors 138 or 138a. When turned on, mechanism 158 causes horn 150 to sound a distinctive signal when the trainee is on base 36. The trainee must then strike a receptor 32 or retreat from base 36 within a number of seconds set on mechanism 158. Otherwise, horn 150 sounds.

The random stop mechanism 160 shown in FIG. 14, is connected to horn 150, weight receptors 138a and timer 154. When set, mechanism 160 causes a distinctive warning tone from horn 150 when the trainee is on the inner circle segment 138a, indicating the simulated attack previously described, and requiring retreat to the outer circle segment 136a in a preset period of time. Otherwise a horn 150 can be made to sound automatically.

A stance trainer mechanism 162 is provided in control panel 144 and is connected with weight detectors 138a, horn 150 and timer 154. The weight ratio between the two detectors 138a and the circles (segments) 136a which is necessary to avoid horn 150 sounding, can be adjusted. The purpose of stance training was previously described.

A printed readout mechanism 164 is provided in panel 144. It records the occurrence, location and passage of time between target blows, and is capable of recording at least four strikes per second. When the printed readout sheet is fed into control panel 144's visual playback mechanism 166, through slot 168, the same lights 44 in panel 40 flash at the same rate in the same sequence as did during the original sequence of strikes which were recorded on the printout sheet. The playback speed can be increased or decreased by a playback speed control 170. It will be understood that the playback mechanism can be very useful in studying a proper strike sequence.

Control panel 144 further includes a contact programmer mechanism 172 having a sequence retention panel 174 containing a plurality of buttons 176 programmable in sequence. Programmer 172 is connected to receptors 32, timer 154 and horn 150. When it is started, horn 150 sounds and timer 154 begins. The sequence punched out on buttons 176 must be followed within a preset amount of time which is recorded on a visual display (not shown). Programmer 172 can also be set to sound horn 150 if the proper sequence is not carried out within the preset time. The "auto repeat" portion of programmer 172 enables the exercise to be repeated, initiated as in the original exercise, by horn 150 sounding, and requiring the same sequence of strikes within the preset period of time.

It will be understood that sequence noting and retention components of programmer 172 can be any conventional components, as can the circuitry relays and other components for the previously described mechanisms used in control panel 144. Other mechanisms than those described in panel 144 can also be employed to facilitate maximum use of device 20 and maximum benefits in self defense training.

Device 20 is durable, highly efficient, novel and advantageous, providing valuable training which cannot be obtained in any other practical way. Other features and advantages are as set forth in the foregoing.

Various modifications, alterations, changes and additions can be made in the improved training device of the invention and in its components and parameters. All such modifications, changes, alterations and additions as are within the scope of the appended claims form part of the present invention.

What is claimed is:

1. An improved device for use in self defense training, said device comprising, in combination:
    a. a training dummy having a human appearance and configuration;
    b. means movably supporting said dummy, said means including a base having weight detecting means to detect the presence of a person standing thereon and to activate means to move said dummy in response to weight detection;
    c. pressure responsive means disposed at various target locations within said dummy adjacent the surface thereof; and,
    d. signaling means interconnected to said pressure response means for signaling when said pressure responsive means are hit during practice with said dummy.

2. The improved device of claim 1 wherein said dummy has jointed and articulated limbs movable to and lockable in desired positions.

3. The improved device of claim 2 wherein said dummy comprises a frame and resilient material disposed over said frame, and wherein said signaling means are remote means connected to said pressure responsive means by leads passing through said support means.

4. The improved device of claim 2 wherein said support means includes a flexible extendible post and said dummy is rotatable thereon.

5. The improved device of claim 2 wherein said support means includes a generally vertical post connected at one end to the lower portion of said dummy and at the opposite end to said base which is generally horizontally extending.

6. The improved device of claim 5 wherein said post is flexible, wherein shock absorbing means are connected to said post and base, and wherein said dummy is articulated at its waist portion.

7. The improved device of claim 2 wherein shock absorbing means are disposed in said dummy to protect at least one of its appendages.

8. The improved device of claim 7 wherein said appendages include the head of said dummy, and wherein shock absorbing means are also disposed in said dummy in its waist region and connected to said support means which comprises a post.

9. The improved device of claim 2 wherein said pressure responsive means in said dummy include means for discriminating between light pressure and hard pressure hits thereon during practice with said dummy.

10. The improved device of claim 9 wherein each of said pressure responsive means includes a movable pressure receptor and a pair of contacts spaced along the path of movement of said receptor upon receiving a blow, said contacts being connected to said signaling means.

11. The improved device of claim 10 wherein said signaling means comprises an electrically operated remote display panel having a plurality of separate lights activated by said individual contacts to indicate the location and intensity of said blows.

12. The improved device of claim 11 wherein said panel includes means for controlling the response of said lights to said contacts, relative to the desired mode of use of said dummy.

13. The improved device of claim 2 wherein said pressure responsive means in said dummy include individual movable pressure receptors and a separate contact for each receptor activatable when said receptor is moved by a blow into contact therewith, said contacts being individually connected to said signaling means.

14. The improved device of claim 13 wherein said signaling means comprises an electrically operated remote display panel having a plurality of separate visual display means activatable by said individual contacts to indicate the location of said blows.

15. The improved device of claim 14 wherein said contacts are connected to a resettable hit counter in said panel.

16. The improved device of claim 14 wherein said panel includes programming means to demonstrate visually through said signaling means a programmed sequence of blows, as in instructional aid.

17. The improved device of claim 15 wherein said contacts are connected to a resettable hit timer in said panel.

18. The improved device of claim 17 wherein said timer and counter are interconnected to provide indication of the number of hits/unit time.

19. The improved device of claim 17 wherein said panel includes printed readout means to record a blow sequence transmitted to said panel from said contacts.

20. The improved device of claim 19 wherein said panel includes visual playback means to visually replay a blow sequence recorded by said panel.

21. The improved device of claim 17 wherein said panel includes warning means and sequence means, the latter being connected to said visual display means, said time and said warning means and programmable to provide a hit sequence which must be followed during use of said dummy with a preset time in order to avoid activating said warning means.

22. An improved device for use in self defense training, said device comprising, in combination:
a. a training dummy having a human appearance and configuration, and jointed and articulated limbs movable to and lockable in desired positions;
b. means movably supporting said dummy, said means including a generally vertical post connected at one end to the lower portion of said dummy and at the opposite end to a generally horizontally extending base, said base including weight detecting means to detect the presence of a person standing thereon and to activate means to move said dummy in response to weight detection;
c. pressure responsive means disposed at various target locations within said dummy adjacent the surface thereof; and,
d. Signaling means interconnected to said pressure responsive means for signaling when said pressure responsive means are hit during practice with said dummy.

23. The improved device of claim 22 wherein said base is divided into a plurality of independent segments, each of which includes separate weight detection means.

24. The improved device of claim 23 wherein said weight detecting means are connected to remote at least one of control means and remote signal means.

25. The improved device of claim 24 wherein said post is connected to power means for rapidly rotating said post, wherein said power means are connected to said remote control means wherein said segments radiate from said post, wherein said separate weight detection means are connected to said remote control means to cause said power means to rapidly rotate said post so as to cause said dummy to face a given segment when said segment bears a predetermined weight, as when a person stands thereon.

26. The improved device of claim 25 wherein said device includes safety cut-out means disposed in the leg articulations of said dummy and connected to said weight detection means, said control means and said power means to inactivate said power means to when at least one of said legs is extended and weight is placed on one of said segments in the path of said extended leg during said rotation.

27. The improved device of claim 23 wherein said segments comprise a pair of circles, one spaced within the other and both around said post, wherein said remote signal means give a signal when both said circles are stood upon, as by 1 foot in each circle, and the distribution of weight placed on said circles is between predetermined adjustable limits.

28. The improved device of claim 22 wherein said post is connected to power means for rapidly rotating said post, wherein said weight detecting means and power means are connected to remote control means and remote signal means programmable to provide an alert signal before sudden rotation of said post when a person is standing on said weight detecting means, whereby sudden attacks are simulated with said dummy.

29. The improved device of claim 22 wherein said weight detecting means are connected to remote programmable timing means and remote signal means for practice of rapid self defense action when a person activates said weight detecting means by standing on said base.

* * * * *